United States Patent
Alkhatib et al.

(10) Patent No.: US 9,615,920 B2
(45) Date of Patent: Apr. 11, 2017

(54) COMMISSURE ATTACHMENT FEATURE FOR PROSTHETIC HEART VALVE

(71) Applicant: St. Jude Medical, Cardiology Division, Inc., St. Paul, MN (US)

(72) Inventors: Yousef F. Alkhatib, Edina, MN (US); Peter Nicholas Braido, Wyoming, MN (US)

(73) Assignee: St. Jude Medical, Cardiology Divisions, Inc., St. Paul, MN (US)

( * ) Notice: Subject to any disclaimer, the term of this patent is extended or adjusted under 35 U.S.C. 154(b) by 0 days.

(21) Appl. No.: 13/781,140

(22) Filed: Feb. 28, 2013

(65) Prior Publication Data

US 2014/0005775 A1 Jan. 2, 2014

Related U.S. Application Data

(60) Provisional application No. 61/666,353, filed on Jun. 29, 2012.

(51) Int. Cl.
*A61F 2/24* (2006.01)

(52) U.S. Cl.
CPC .......... *A61F 2/2403* (2013.01); *A61F 2/2415* (2013.01); *A61F 2/2418* (2013.01); *A61F 2220/005* (2013.01); *A61F 2220/0075* (2013.01); *A61F 2230/0054* (2013.01); *A61F 2230/0067* (2013.01); *A61F 2230/0069* (2013.01)

(58) Field of Classification Search
CPC ................................. A61F 2/24; A61F 2/2403
USPC .................................................. 623/2.1–2.19
See application file for complete search history.

(56) References Cited

U.S. PATENT DOCUMENTS

| | | | |
|---|---|---|---|
| 3,657,744 | A | 4/1972 | Ersek |
| 4,275,469 | A | 6/1981 | Gabbay |
| 4,491,986 | A | 1/1985 | Gabbay |
| 4,759,758 | A | 7/1988 | Gabbay |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report and Written Opinion for Application No. PCT/US2013/048169 dated Oct. 25, 2013.

(Continued)

*Primary Examiner* — Suzette J Gherbi
(74) *Attorney, Agent, or Firm* — Lerner, David, Littenberg, Krumholz & Mentlik, LLP

(57) ABSTRACT

A prosthetic heart valve includes a collapsible and expandable stent having a proximal end, a distal end, an annulus section adjacent the proximal end and an aortic section adjacent the distal end, the stent including a plurality of struts. A plurality of commissure features is disposed on the stent and coupled to selected ones of the struts, each commissure feature including a body having a proximal end and a distal end, and at least one eyelet in the body. The heart valve further includes a collapsible and expandable valve assembly including a plurality of leaflets. At least one leaflet is connected to the at least one eyelet and to at least one of the selected ones of the struts via a suture pattern.

12 Claims, 6 Drawing Sheets

(56) References Cited

U.S. PATENT DOCUMENTS

| | | | |
|---|---|---|---|
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,329,278 B2 | 2/2008 | Seguin et al. | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 6/2013 | Braido | |
| 8,808,366 B2* | 8/2014 | Braido | A61F 2/2418 623/1.26 |
| 8,882,831 B2* | 11/2014 | Alkhatib | A61F 2/2418 623/2.17 |
| 8,932,343 B2* | 1/2015 | Alkhatib | A61F 2/2418 623/1.15 |
| 9,011,527 B2* | 4/2015 | Li | A61F 2/2412 623/1.26 |
| 9,039,759 B2* | 5/2015 | Alkhatib | A61F 2/2418 623/1.26 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147179 A1 | 6/2008 | Cai et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0228264 A1 | 9/2008 | Li et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0098800 A1* | 4/2011 | Braido | A61F 2/2412 623/1.16 |
| 2011/0295363 A1* | 12/2011 | Girard | A61F 2/2412 623/1.26 |

(56) References Cited

U.S. PATENT DOCUMENTS

| | | | |
|---|---|---|---|
| 2012/0071969 A1* | 3/2012 | Li | A61F 2/2412 623/2.17 |
| 2012/0197391 A1* | 8/2012 | Alkhatib | A61F 2/2418 623/2.18 |
| 2014/0005775 A1* | 1/2014 | Alkhatib | A61F 2/2418 623/2.18 |
| 2014/0005776 A1* | 1/2014 | Braido | A61F 2/2418 623/2.18 |
| 2014/0005777 A1* | 1/2014 | Anderl | A61F 2/2418 623/2.18 |
| 2014/0018915 A1* | 1/2014 | Biadillah | A61F 2/2418 623/2.17 |
| 2014/0107772 A1* | 4/2014 | Li | A61F 2/2418 623/2.17 |
| 2014/0222140 A1* | 8/2014 | Schreck | A61F 2/2418 623/2.14 |
| 2015/0057747 A1* | 2/2015 | Li | A61F 2/2418 623/2.18 |
| 2015/0066141 A1* | 3/2015 | Braido | A61F 2/2418 623/2.17 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| JP | 2011509805 A | 3/2011 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2009/042196 A2 | 4/2009 |
| WO | 2009053497 A1 | 4/2009 |
| WO | 2010008548 A2 | 1/2010 |
| WO | 2010096176 A1 | 8/2010 |
| WO | 2010098857 A1 | 9/2010 |
| WO | 2012032187 A1 | 3/2012 |

OTHER PUBLICATIONS

Catheter-implanted prosthetic heart valves, Knudsen, L.L., et al., The International Journal of Artificial Organs, vol. 16, No. 5 1993, pp. 253-262.
Design U.S. Appl. No. 29/375,243, filed Sep. 20, 2010.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, Overview of PRE-CE Mark Transcatheter Aortic Valve Technologies, Euro PCR (powerpoint)—dated May 25, 2010?
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.

* cited by examiner

COMMISSURE ATTACHMENT FEATURE FOR PROSTHETIC HEART VALVE

CROSS REFERENCE TO RELATED APPLICATION

This application claims the benefit of the filing date of U.S. Provisional Patent Application No. 61/666,353 filed Jun. 29, 2012, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having superior commissure feature attachments.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

Despite the various improvements that have been made to collapsible prosthetic heart valves, conventional valves and systems suffer from some shortcomings. For example, conventional prosthetic valves may fail at high stress regions including the leaflet-commissure feature junction. Failure may, for example, include tearing of the sutures and/or the leaflets. To reduce the risk of failure, the optimal valve would more adequately secure the leaflets to the stent without adding unwanted bulk to the overall structure.

There therefore is a need for further improvements to collapsible prosthetic heart valves, and in particular, self-expanding prosthetic heart valves. Among other advantages, the present invention may address one or more of these needs.

SUMMARY OF THE INVENTION

In some embodiments, a prosthetic heart valve includes a collapsible and expandable stent having a proximal end, a distal end, an annulus section adjacent the proximal end and an aortic section adjacent the distal end, the stent including a plurality of struts. A plurality of commissure features may be disposed on the stent and coupled to selected ones of the struts, each commissure feature including a body having a proximal end and a distal end, and at least one eyelet in the body. The valve further includes a collapsible and expandable valve assembly, including a plurality of leaflets, at least one of the leaflets being connected to at least one eyelet and to at least one of the selected ones of the struts via a suture pattern.

In some examples, selected ones of the struts includes two struts coupled to the distal end of the body, and the at least one leaflet is connected to the two struts. Selected ones of the struts may also include two struts coupled to the proximal end of the body, and the at least one leaflet is connected to the two struts. Selected ones of the struts may further includes two additional struts coupled to the proximal end of the body, and the at least one leaflet is further connected to the two additional struts.

In some examples, each body has two eyelets and a central rib formed between the two eyelets. The suture pattern may include loops of suture around the central rib. The suture pattern may include four loops of suture around the central rib. Two leaflets may be connected to each commissure feature. The suture pattern may be symmetrical about a central axis passing through the body between the proximal and distal ends of the body.

In some embodiments, a method of assembling a prosthetic heart valve includes providing a collapsible and expandable stent having a proximal end, a distal end, an annulus section adjacent the proximal end and an aortic section adjacent the distal end, the stent include a plurality of struts and a plurality of commissure features disposed on the stent and coupled to selected ones of the struts, each commissure feature including a body having a proximal end and a distal end, and at least one eyelet in the body. A collapsible and expandable valve assembly is coupled to the stent, the valve assembly including a plurality of leaflets, and the coupling step including connecting at least one of the leaflets to the at least one eyelet and to at least one of the selected ones of the struts via a suture pattern.

In some examples, selected ones of the struts include two struts coupled to the distal end of the body, and the coupling step includes connecting the at least one leaflet to the two struts. Selected ones of the struts may also include two struts coupled to the proximal end of the body, and the coupling step includes connecting the at least one leaflet to the two struts. Selected ones of the struts may further include two additional struts coupled to the proximal end of the body, and the coupling step further includes connecting the at least one leaflet to the two additional struts. The coupling step may include connecting two leaflets to each commissure feature. The coupling step may include coupling the at least one leaflet to the body using a suture pattern that is symmetrical about a central axis passing through the body between the proximal and distal ends of the body.

BRIEF DESCRIPTION OF THE DRAWINGS

Various embodiments of the present invention are described herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
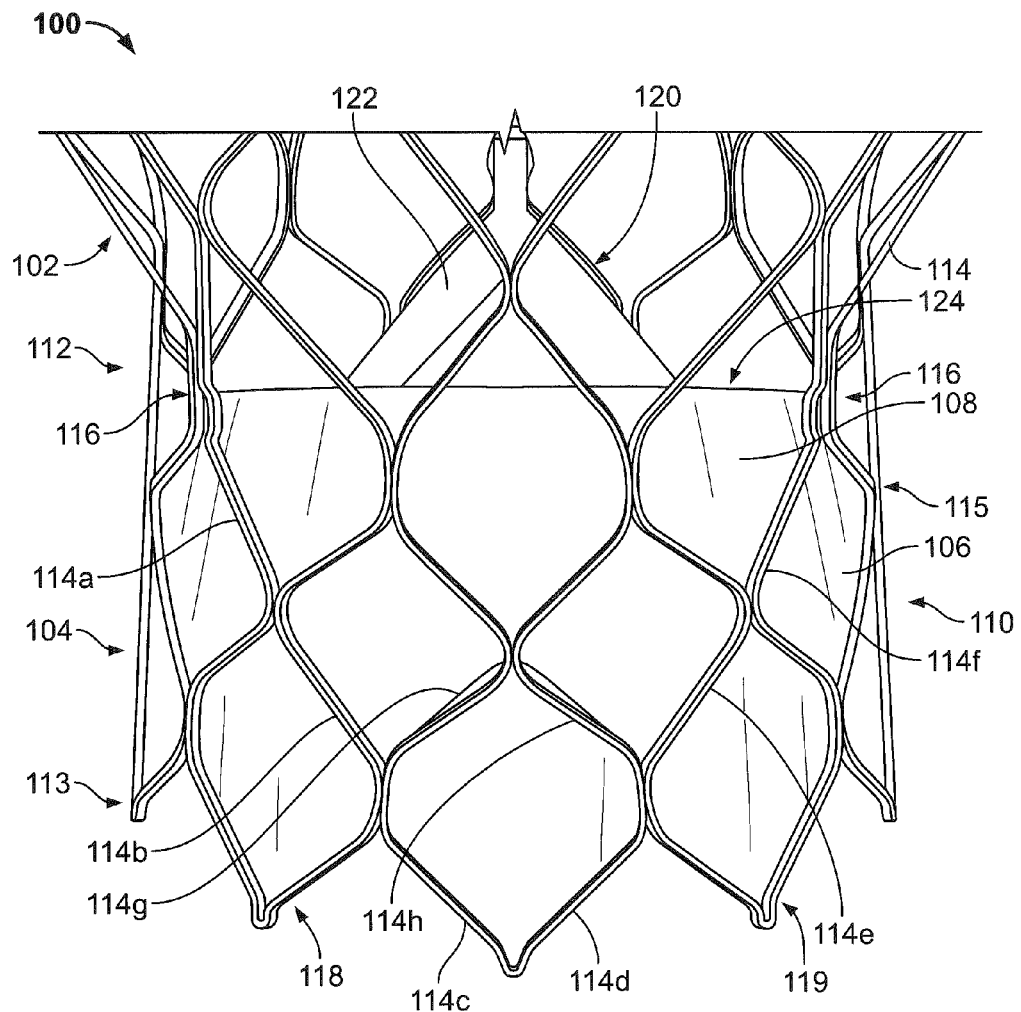
FIG. 1 is a partial side elevational view of a prosthetic heart valve including a valve assembly and a stent.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110, an aortic section (not shown) and a transition section (not shown) disposed between the annulus section and the aortic section. Each of the annulus section 110, the aortic section and the transition section of the stent 102 includes a plurality of cells 112 connected to one another around the stent. The annulus section 110, and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features 116 connecting at least two cells 112 in the longitudinal direction of the stent 102. The commissure features 116 may include eyelets for facilitating the suturing of a valve assembly 104 to the sent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester. In at least some examples, portions of valve assembly 104, a cuff and the suture used may include an ultra high molecular weight polyethylene, such as FORCE FIBER®.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. The cuff 106 and/or the sutures used to attach the valve assembly 104 to stent 102 may be formed from or include ultra-high-molecular-weight polyethylene. FIG. 1 shows cuff 106 disposed on the lumenal surface of annulus section 110 so as to cover part of the annulus section while leaving another part thereof uncovered. The cuff 106 may be attached to strut 102 by one or more strings or sutures passing through the cuff and around selected struts 114 of the stent. The valve assembly 104 may further include a plurality of leaflets 108 which collectively function as a one-way valve. A first edge 122 of each leaflet 108 may be attached to the stent 102 between two adjacent commissure features 116 by any suitable attachment means, such as suturing, stapling, adhesives or bonding via laser, ultrasound or heat as well as any other suitable method. For example, the first edge 122 of each leaflet 108 may be sutured to the stent 102 by passing strings or sutures through the cuff 106 of the valve assembly 104. The leaflets 108 may be attached to the stent 102 along at least some struts 114 of the stent and through the eyelets in the commissure features 116 to enhance the structural integrity of the valve assembly 104. A second or free edge 124 of each leaflet 108 may coapt with the corresponding free edges of the other leaflets, thereby enabling the leaflets to function collectively as a one-way valve.

As shown in FIG. 1, at least one leaflet 108 may be attached to the stent 102 so that its first edge 122 is disposed substantially along specific struts 114a, 114b, 114c, 114d, 114e and 114f located in the annulus section 110 of the stent. That is, the edge 122 is positioned in substantial alignment with struts 114a, 114b, 114c, 114d, 114e, and 114f. Struts 114a, 114b, and 114c may be connected to one another in substantially end-to-end fashion diagonally along three cells 112, beginning with an end of the strut 114a connected to a commissure feature 116 and ending with an end of strut 114c connected to an end of strut 114d. Struts 114c and 114d are part of the same cell 112 and may collectively define a substantially right angle between them. Struts 114*d*, 114*e*, and 114*f* may be connected to one another in substantially end-to-end fashion diagonally along three cells 112, beginning with an end of the strut 114*f* connected to a commissure feature 116 and ending with the connection between an end of strut 114*c* and an end of strut 114*d*.

As discussed above, the leaflets 108 may be attached directly to and supported by the struts 114*a*, 114*b*, 114*c*, 114*d*, 114*e*, and 114*f*, and by commissure features 116, such as by suturing. In such event, the cuff 106 may perform little or no supportive function for the leaflets 108. Hence, the cuff 106 is not subjected to high stresses and is therefore less likely to wear during use. In light of this, the thickness of the cuff may be reduced. Reducing the thickness of the cuff 106 results in a decrease in the volume of the valve assembly 104 in the collapsed condition. This decreased volume is desirable as it enables the prosthetic heart valve 100 to be implanted in a patient using a delivery device that is smaller in cross-section than conventional delivery devices. In addition, since the material forming the stent struts 114 is generally stronger than the material forming the cuff 106, the stent struts 114 may perform the supportive function for the leaflets 108 better than the cuff 106.

In operation, the embodiments of the prosthetic heart valve 100 described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device. During delivery, the prosthetic heart valve is disposed inside the delivery device in the collapsed condition. The delivery device may be introduced into a patient using a transfemoral, transapical, transseptal, transaxillary or other approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

Figure 2A:
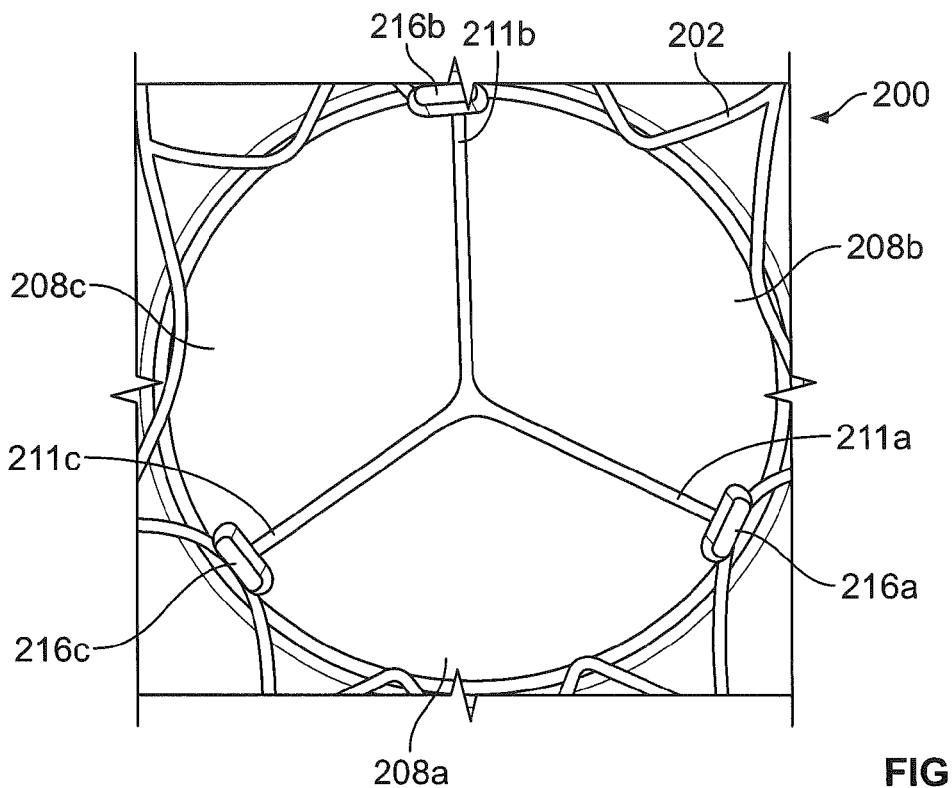
FIG. 2A is an end view of a prosthetic heart valve as seen from the aortic sinus toward the heart and the native valve annulus, the valve having a circular configuration.
Figure 2B:
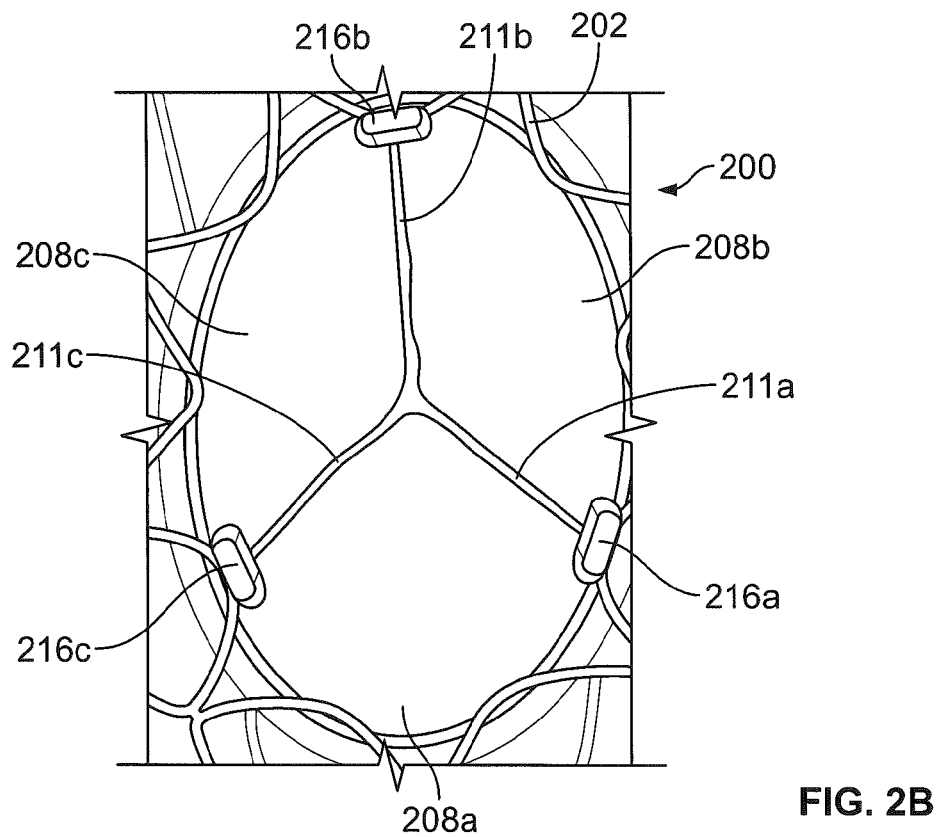
FIG. 2B is an end view of a prosthetic heart valve as seen from the aortic sinus toward the heart and the native valve annulus, the valve having an elliptical configuration.

FIGS. 2A and 2B show an end view of a prosthetic heart valve 200 as seen from the downstream side of the valve assembly, e.g., looking from the aorta or aortic sinus toward the heart and the native valve annulus. As seen in FIG. 2A, the valve assembly includes a stent 202 and valve leaflets 208*a*, 208*b*, and 208*c* attached to the stent and to commissure features 216*a*, 216*b*, and 216*c*. At least one edge of each leaflet 208 is sutured to the stent 202 and to two of the three commissure features 216, leaving at least one edge free to move in response to the pumping of blood. As the blood pressure in the left ventricle increases, the free edges of the leaflets move away from one another to allow blood to flow from the left ventricle to the aorta, following which the free edges move toward one another and coapt to prevent blood from flowing back from the aorta into the left ventricle.

Areas of actual contact between the coaptation sections of adjacent leaflets are referred to herein as the coaptation junctions of the leaflets and are illustrated in FIG. 2A at 211*a*, 211*b*, and 211*c*. The coaptation section of each leaflet may range in size as a particular valve design demands, but generally will be sufficient to provide some tolerance or ability to form a coaptation junction even if the shape of the valve is distorted during placement, as illustrated in FIG. 2B.

The annulus section of prosthetic heart valve 200 has a generally regular cylindrical shape by which is meant that the structure has a generally circular cross-section with a substantially constant diameter along its length. When placed in the annulus of a native heart valve, such as, for example, the tricuspid aortic valve, and expanded, a substantially fluid-tight fit should result. However, the native valve annulus may not be circular, and, in fact, may vary from patient to patient, as may the shape of the aortic sinus or aorta, the angle of the junction between the valve annulus and the aortic sinus, and other local anatomical features. When prosthetic heart valve 200 is deployed and expanded, it must accommodate these anatomical variations in order to function properly. This may result in a distortion in the shape of stent 202 and/or valve assembly 204, and the repositioning of leaflets 208*a*, 208*b*, and 208*c* relative to one another, which can affect the coaptation junctions 211*a*, 211*b*, and 211*c*.

As the stent of a collapsible prosthetic heart valve distorts during implantation, during beating of the heart, or because of irregularities in the patient's anatomy or the condition of the native valve, such distortion may be translated to the valve assembly, such that not all of the valve leaflets meet to form effective coaptation junctions. This can result in leakage or regurgitation and other inefficiencies which can reduce cardiac performance. Moreover, if the prosthetic valve is not placed optimally and the valve leaflets are not coapting as intended, other long term effects, such as uneven wear of the individual leaflets, can be postulated.

As shown in FIG. 2B, ideally, valve leaflets 208*a*, 208*b*, and 208*c* fully coapt despite the distortion of the annulus section (hidden behind the valve leaflets in this figure) into a more elongated or elliptical configuration. As will be appreciated, the distortion of the annulus section affects the relative positions of commissure features 216*a-c*, as well as the positions of leaflets 208*a-c* relative to one another. The ability of the valve leaflets 208*a-c* to fully coapt despite this distortion enables prosthetic valve 200 to function in the manner intended.

Figure 3:
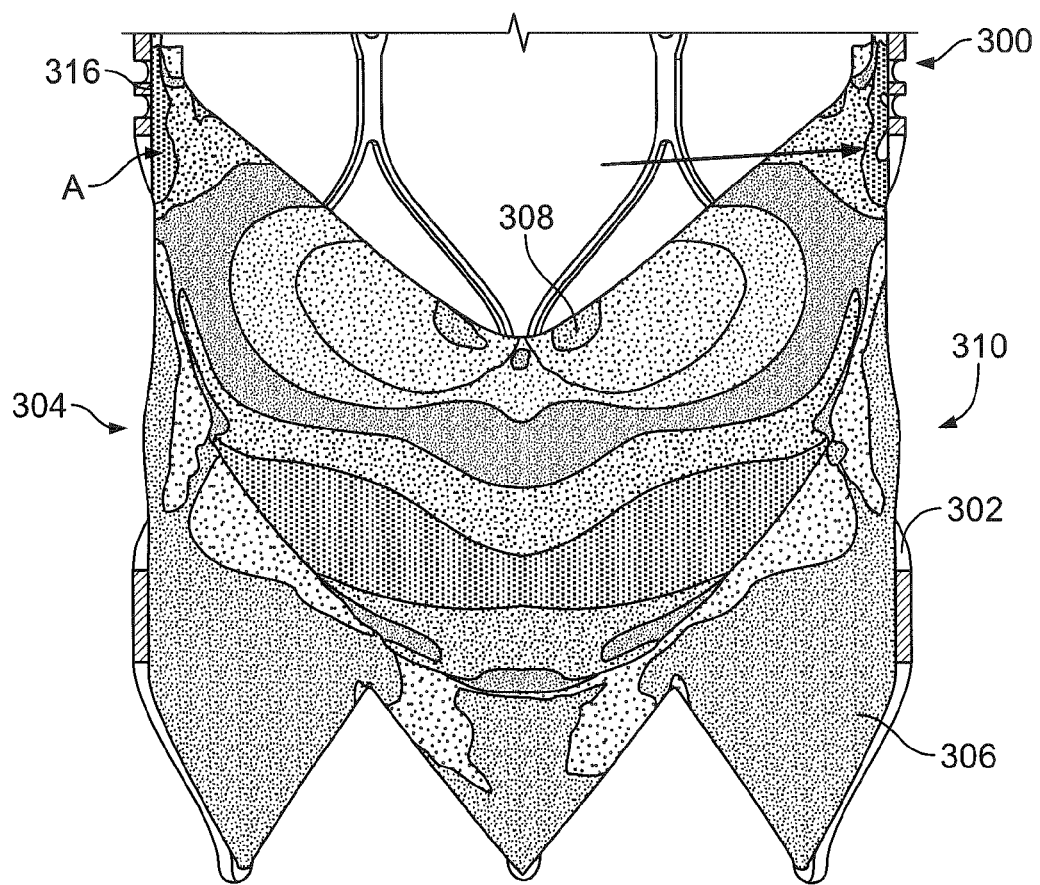
FIG. 3 is a partial side elevational view of the prosthetic heart valve of FIG. 1 depicting areas of high stress on the valve assembly.

Less than ideal native valve geometry may increase the stresses on certain portions of the prosthetic heart valve. FIG. 3 is a partial side view of a prosthetic heart valve 300 having a stent 302 and a valve assembly 304 disposed in the annulus section 310 of the stent. Within the heart valve 300, leaflets 308 are attached to cuff 306 via sutures. Specifically, FIG. 3 shows the load distribution in the valve assembly. When leaflets 308 coapt to form a closed configuration, load is transferred from the leaflet structure to the leaflet-commissure feature junction as indicated by "A". The load distribution diagram shows that high point loads are generated at region "A" where the leaflets and/or the cuff are joined to the commissure feature 316. If the point loads at regions "A" are sufficiently high, the leaflets may tear from the commissure feature. Thus, regions A may be prone to wear. Moreover, if loads are not properly distributed, the valve may wear at another location.

Figure 4:
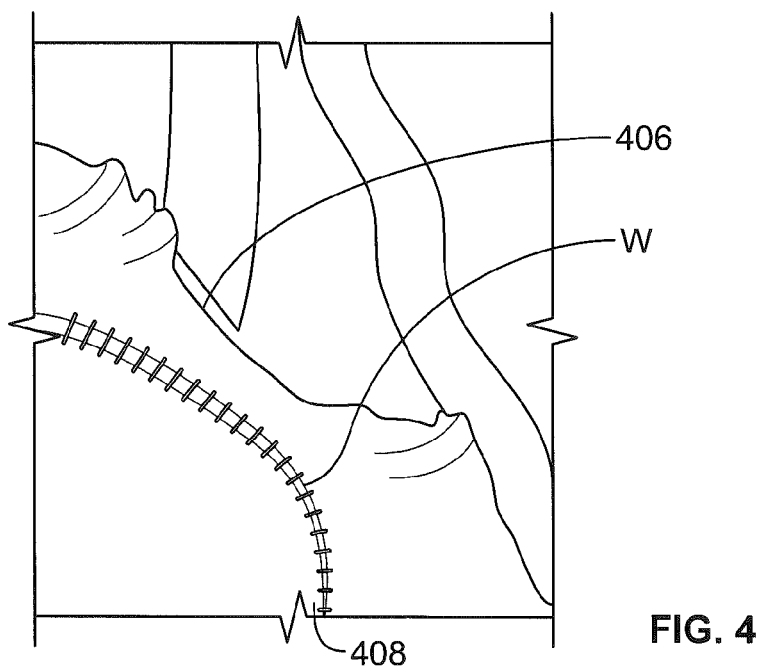
FIG. 4 is an enlarged top perspective view of wear along a portion of the collapsible prosthetic heart valve at the suture junction with the cuff.

FIG. 4 is an enlarged top perspective view of a portion of the collapsible prosthetic heart valve showing a possible location of wear. As seen from this view, at wear region W, the leaflet 408 may become detached from cuff 406. Such wear may occur by separation of the cuff 406, the leaflet 408, the sutures attaching the leaflet to the cuff, or any combination thereof. Superior attachment of the leaflets to the commissure features may better distribute stresses to the stent structure, decreasing the likelihood of tissue or suture wear and improving durability.

Features of this aspect of the present invention will be described in connection with the commissure attachment feature 500 shown in FIG. 5. It will also be noted that while the inventions herein are predominantly described with respect to a tricuspid valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Figure 5:
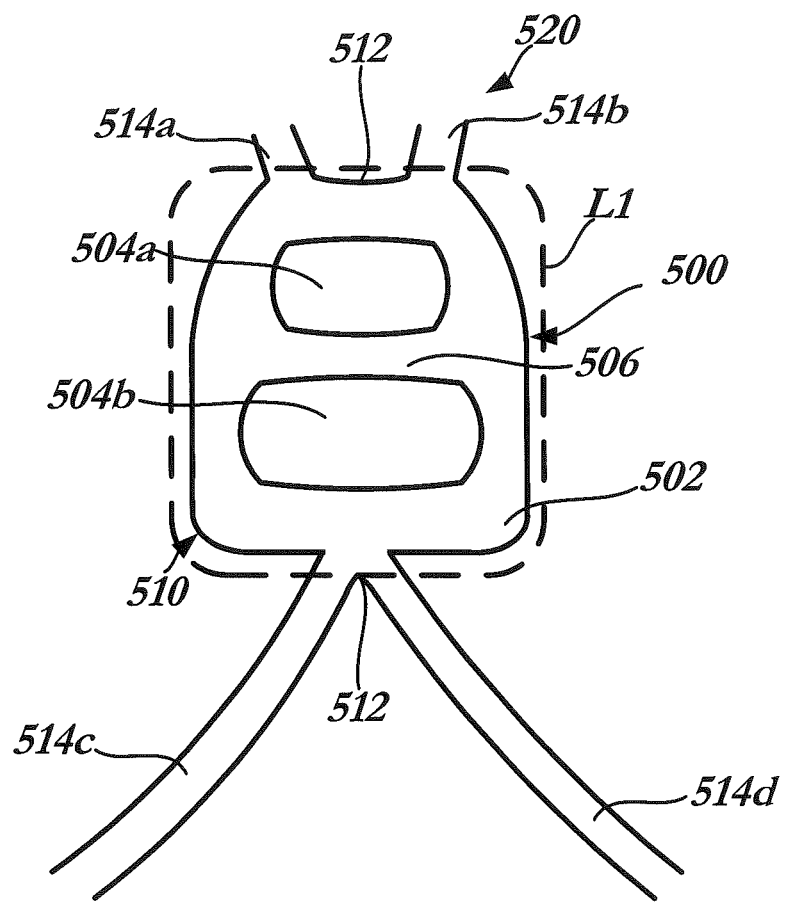
FIG. 5 is an enlarged schematic side view of a commissure feature according to the present invention.

FIG. 5 illustrates a commissure feature 500 coupled to struts 514 for attaching a valve assembly to the stent. Commissure feature 500 may be formed of a body 502 having a proximal end 510 and a distal end 520. Body 502 may be generally trapezoidal near the proximal end 510 and may include an oval portion near the distal end 520. Any number of eyelets 504 may be provided in body 502, including one, two, three, four, five or six eyelets. Eyelets 504 may be disposed in rows or columns and may be formed with the same or different shapes. Each pair of eyelets 504 may be separated by a rib for attaching a suture to the commissure feature 500. As shown in FIG. 5, commissure feature 500 has two eyelets, an upper eyelet 504a and a lower eyelet 504b, separated by a rib 506.

As seen in FIG.5, commissure feature 500 is coupled to four struts 514a-d, two of which converge at each end of the body 502. For example, struts 514a and 514b merge near the top of body 502. The meeting point where two struts 514 merge is referred to as an ancon 512. Thus, commissure feature 500 includes two ancons 512, one at the top of body 502 between struts 514a and 514b, and a second at the bottom of body 502 between struts 514c and 514d.

Leaflets (not shown) may be attached to commissure feature 500 by passing sutures through eyelets 504 and/or around struts 514. In this manner, load may be distributed across the area of commissure feature 500. Specifically, stress from the leaflets is distributed across substantially the entirety of area L1 of the commissure feature 500. Thus, commissure feature 500 is sized to be as large as practical so as to have a large area to distribute stress across, yet small enough to allow for the manufacture of a relatively short stent having as small a circumferential crimp profile as possible, while providing substantial flexibility during implantation.

Figure 6B:
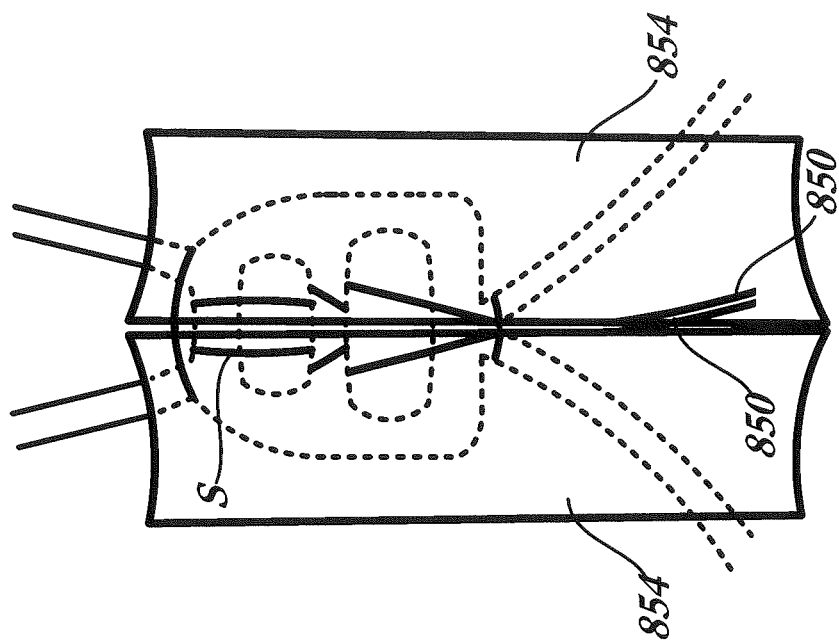
FIGS. 6A and 6B are enlarged schematic side views of a suture pattern attaching leaflets to a commissure feature as shown from the ablumenal side and the lumenal side of the valve, respectively.
Figure 6A:
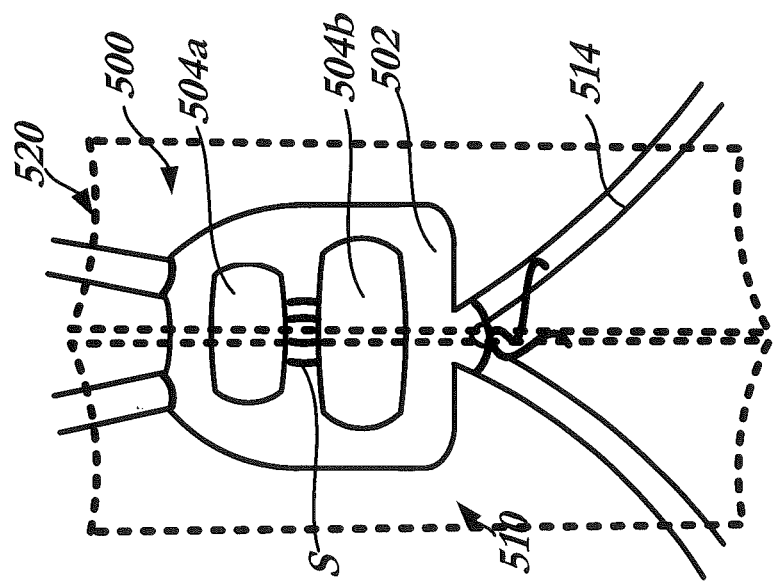
Figure 6C:
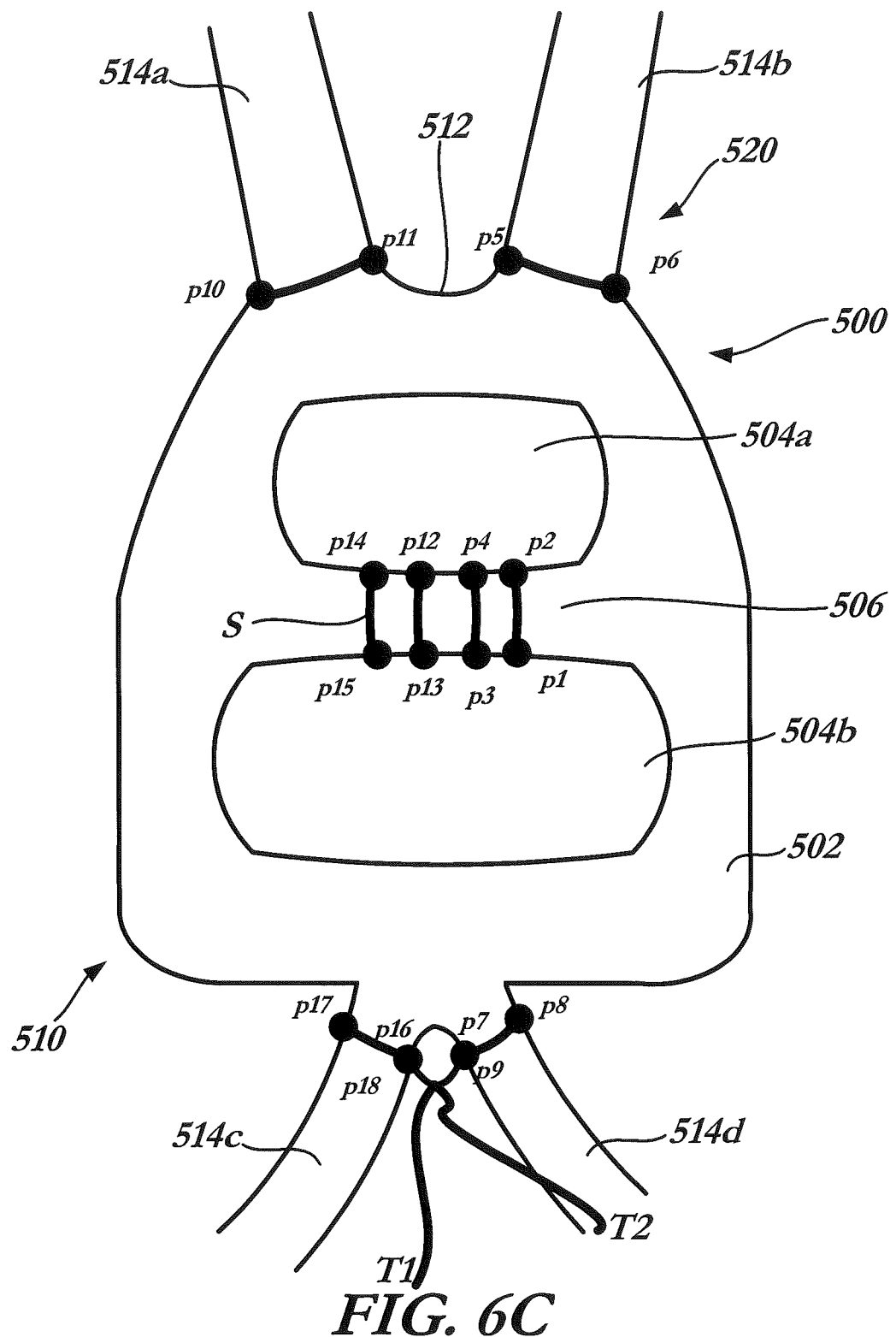
FIG. 6C is a highly enlarged, schematic side view showing the suture pattern coupling the leaflets to the commissure feature of FIGS. 6A and 6B.

The suture pattern attaching the leaflets to the commissure feature may reduce the risk of failure of the valve. One example of such a suture pattern according to the present invention is illustrated in FIGS. 6A-C. FIG. 6A illustrates the leaflet-commissure feature combination as seen from the ablumenal side of a valve assembly, while FIG. 6B illustrates the same combination as seen from the lumenal side of the valve assembly.

Each leaflet includes a tab 854 at each point at which the two edges of the leaflet intersect. These tabs 854 are used to join the leaflets to the commissure features 500 of the stent. As seen in FIG. 6B, two tabs 854 of two different leaflets 850 are attached to commissure feature 500 using a single or multiple sutures. As described herein, a single suture S attaches leaflets 850 to commissure feature 500. It will be understood, however, that multiple sutures may be used to attach the leaflets to the commissure feature. For example, one suture may attach a first leaflet 850 to commissure feature 500, while a second, separate suture attaches the second leaflet 850 to commissure feature 500.

The suture pattern and the order of attachment will be described with reference to FIG. 6C, which shows an enlarged view of the leaflet-commissure combination from the ablumenal side of the valve assembly and depicts the suture pattern through several positions p1-16 on the assembly. It will be appreciated that FIG. 6B shows the corresponding suture pattern from the lumenal side of the valve assembly and that the suture pattern may be understood from this view as well.

The suture pattern may begin at any point at or near commissure feature 500 and terminate at any other point. In at least some examples, the suture pattern begins and terminates at the same position. For the sake of illustration, the suture pattern will be described as beginning at point p1, within eyelet 504b. As used herein, with reference to FIG. 6C and other figures showing the ablumenal side of the assembly, the term "out" indicates passing the suture from the lumenal side of the valve through the leaflet tab 854 and past the stent structure to the ablumenal side of the valve, while the term "in" indicates passing the suture from the ablumenal side of the valve past the stent structure and through the leaflet tab 854 to the lumenal side of the valve.

The suture pattern may include two suture tails and may begin by passing the first suture tail out through eyelet 504b at point p1. Suture S may then be advanced in through point p2 in eyelet 504a, back out through point p3 in eyelet 504b and finally in through point p4 in eyelet 504a, essentially forming two loops of sutures around central rib 506. As used herein, the term "central" is used generally to mean that the rib is disposed anywhere between two eyelets, and not at the midpoint. Suture S may then be directed to the distal end 520 of commissure feature 500 and passed out through point p5 adjacent the inner edge of strut 514b, and then in through point p6 located adjacent the outer edge of strut 514b. The second tail of suture S may be directed to the proximal end 510 of commissure feature 500 and passed out through point p7 adjacent the inner edge of strut 514d, in through point p8 adjacent the outer edge of strut 514d, and back out through point p9 at or near point p7 to leave a first free tail T1 extending from point p9. In at least some examples, the inner diameter and outer diameter are asymmetric.

Using the first suture tail, previously at point p6, suture S may be maneuvered toward strut 514a and passed out through point p10 adjacent the outer edge of strut 514a, around the strut, and then in through point p11 adjacent the inner edge of strut 514a. Suture S may then be directed toward rib 506 and passed out through point p12 in eyelet 504a, in through point p13 in eyelet 504b, back out through point p14 in eyelet 504a, and in again through point p15 in eyelet 504b, forming two additional loops around central rib 506. From point p15, suture S may be directed to the proximal end 570 of commissure feature 500 and passed out through point p16 adjacent the inner edge of strut 514c, in through point p17 adjacent the outer edge of strut 514c, and out again through point p18 located at or near point p16 to form a loop around strut 514c and leave a second free tail T2 extending from point p18. Suture S may then be secured by knotting or tying the free tails T1 and T2 together near points p9 and p18 to complete the attachment of leaflets 850 to the commissure feature 500.

As seen in FIG. 6C, one advantage of using commissure attachment feature 500 is that it allows attachments above and/or below the commissure feature at struts 514a-d. Sutures that wrap around struts 514a-d may be wrapped at or near ancons 512. The ability to apply sutures around struts 514 at or near ancons 512 affords a degree of flexibility and compliance in the overall attachment scheme while still effecting a secure attachment of the leaflets 850 to the commissure feature 500. Thus, the attachment of the leaflets 850 to commissure attachment feature 505 is not limited to eyelets 504. As is evident from FIG. 6C, the final suture pattern may be symmetric about a central axis passing through body 502 between struts 514a and 514b on the distal end 520 of the body and between struts 514*c* and 514*d* on the proximal end 510 of the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
  a collapsible and expandable stent having a proximal end, a distal end, an annulus section adjacent the proximal end and an aortic section adjacent the distal end, the stent including a plurality of struts;
  a plurality of commissure features disposed on the stent and coupled to selected ones of the struts, each commissure feature including a body having a proximal end adjacent the annulus section and a distal end adjacent the aortic section, and at least one eyelet in the body, the body being coupled to upper struts near the aortic section; and
  a collapsible and expandable valve assembly, including a plurality of leaflets, at least one of the leaflets being connected to the at least one eyelet and to at least one of the upper struts via a suture pattern, wherein the struts further include two lower struts coupled to the proximal end of the body, and the at least one leaflet is further connected to the two lower struts.

2. The prosthetic heart valve of claim 1, wherein two leaflets are connected to each commissure feature.

3. The prosthetic heart valve of claim 1, wherein the suture pattern is symmetrical about a central axis passing through the body between the proximal and distal ends of the body.

4. The prosthetic valve of claim 1, wherein the suture pattern further includes two tails knotted together adjacent one of the upper struts and the lower struts.

5. A prosthetic heart valve, comprising:
  a collapsible and expandable stent having a proximal end, a distal end, an annulus section adjacent the proximal end and an aortic section adjacent the distal end, the stent including a plurality of struts;
  a plurality of commissure features disposed on the stent and coupled to selected ones of the struts, each commissure feature including a body having a proximal end adjacent the annulus section and a distal end adjacent the aortic section, and at least one eyelet in the body, the body being coupled to upper struts near the aortic section; and
  a collapsible and expandable valve assembly, including a plurality of leaflets, at least one of the leaflets being connected to the at least one eyelet and to at least one of the upper struts via a suture pattern;
  wherein each body has two eyelets and a central rib formed between the two eyelets, and wherein the suture pattern includes loops of suture around the central rib.

6. The prosthetic heart valve of claim 5, wherein the suture pattern includes four loops of suture around the central rib.

7. The prosthetic heart valve of claim 5, wherein the suture pattern begins by being coupled to the central rib, then a first of the upper struts, then a first of the lower struts, then a second of the upper struts, then the central rib a second time, and then a second of the lower struts.

8. A method of assembling a prosthetic heart valve, comprising:
  providing a collapsible and expandable stent having a proximal end, a distal end, an annulus section adjacent the proximal end and an aortic section adjacent the distal end, the stent including a plurality of struts and a plurality of commissure features disposed on the stent and coupled to upper struts adjacent the aortic section, each commissure feature including a body having a proximal end adjacent the annulus section and a distal end adjacent the aortic section, and at least one eyelet in the body, the body being coupled to upper struts near the distal end of the body, and to two lower struts near the proximal end of the body; and
  coupling a collapsible and expandable valve assembly to the stent, the valve assembly including a plurality of leaflets, and the coupling step including connecting at least one of the leaflets to the at least one eyelet and to at least one of the upper struts via a suture pattern;
  wherein the coupling step includes connecting the at least one leaflet to the two lower struts.

9. The method of claim 8, wherein the coupling step includes connecting two leaflets to each commissure feature.

10. The method of claim 8, wherein the coupling step includes coupling the at least one leaflet to the body using a suture pattern that is symmetrical about a central axis passing through.

11. A method of assembling a prosthetic heart valve, comprising:
  providing a collapsible and expandable stent having a proximal end, a distal end, an annulus section adjacent the proximal end and an aortic section adjacent the distal end, the stent including a plurality of struts and a plurality of commissure features disposed on the stent and coupled to upper struts adjacent the aortic section, each commissure feature including a body having a proximal end adjacent the annulus section and a distal end adjacent the aortic section, and at least one eyelet in the body, the body being coupled to upper struts near the distal end of the body; and
  coupling a collapsible and expandable valve assembly to the stent, the valve assembly including a plurality of leaflets, and the coupling step including connecting at least one of the leaflets to the at least one eyelet and to at least one of the upper struts via a suture;
  wherein each body has two eyelets and a central rib formed between the two eyelets, and wherein the suture pattern includes loops of suture around the central rib.

12. The method of claim 11, wherein the suture pattern includes four loops of suture around the central rib.

* * * * *